(12) United States Patent
Shams et al.

(10) Patent No.: US 9,782,981 B2
(45) Date of Patent: Oct. 10, 2017

(54) METHOD AND ASSEMBLY FOR PRINTING ONTO A BALLOON BLANK

(71) Applicants: Aamer Shams, Feltham (GB); Kazveen Aamer, Feltham (GB)

(72) Inventors: Aamer Shams, Feltham (GB); Kazveen Aamer, Feltham (GB)

(*) Notice: Subject to any disclaimer, the term of this patent is extended or adjusted under 35 U.S.C. 154(b) by 1025 days.

(21) Appl. No.: 13/924,564

(22) Filed: Jun. 22, 2013

(65) Prior Publication Data

US 2013/0287952 A1     Oct. 31, 2013

Related U.S. Application Data

(63) Continuation-in-part of application No. PCT/GB2011/001751, filed on Dec. 21, 2011.

(30) Foreign Application Priority Data

Dec. 22, 2010   (GB) .................................. 1021743.8
Sep. 28, 2011   (GB) .................................. 1116672.5

(51) Int. Cl.
| | |
|---|---|
| *B41J 11/00* | (2006.01) |
| *C05G 3/00* | (2006.01) |
| *C07C 273/02* | (2006.01) |
| *C05C 9/00* | (2006.01) |
| *A63H 27/10* | (2006.01) |
| *B41J 3/407* | (2006.01) |

(52) U.S. Cl.
CPC .............. *B41J 11/00* (2013.01); *A63H 27/10* (2013.01); *B41J 3/407* (2013.01); *C05C 9/005* (2013.01); *C05G 3/0058* (2013.01); *C07C 273/02* (2013.01); *A63H 2027/1025* (2013.01)

(58) Field of Classification Search
None
See application file for complete search history.

(56) References Cited

U.S. PATENT DOCUMENTS

2010/0282625 A1*   11/2010   Lang .................... A63H 27/10
                                                                        206/223

FOREIGN PATENT DOCUMENTS

GB        WO 2010007398 A2 *   1/2010   ............. A63H 27/10

* cited by examiner

*Primary Examiner* — Michael Wieczorek
*Assistant Examiner* — Bradford Gates
(74) *Attorney, Agent, or Firm* — Invention to Patent Services; Alex Hobson

(57) ABSTRACT

The invention describes a method of printing onto a balloon that includes the steps of: coating the printable outer surface of a balloon with a primer material; attaching the balloon about a supporting substrate to form a balloon blank; flattening the printable outer surface of the balloon on the upper surface of the substrate; attaching a first tab on a first end of the balloon blank; attaching a second tab on a second end opposite the first end of the balloon blank; applying the balloon blank to a printer, via the first tab, which in use prints a first image onto the printable surface; and moving the balloon blank back through the printer via the second tab, which in use prints a second image onto the printable surface.

9 Claims, 6 Drawing Sheets

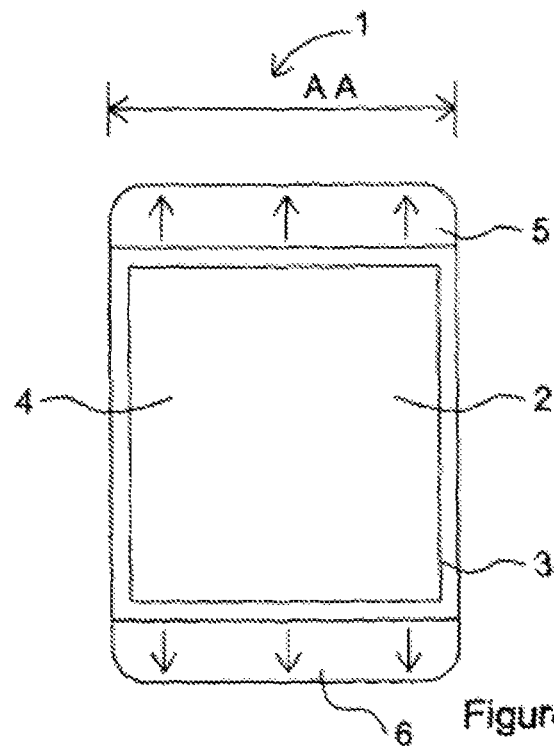
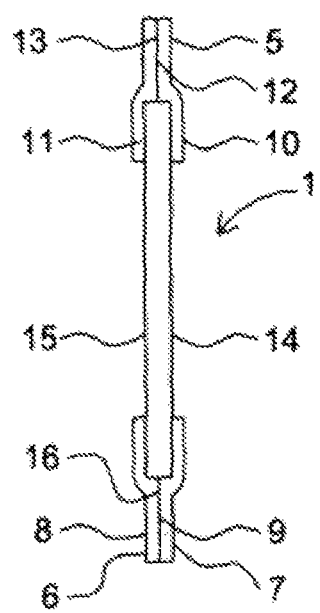 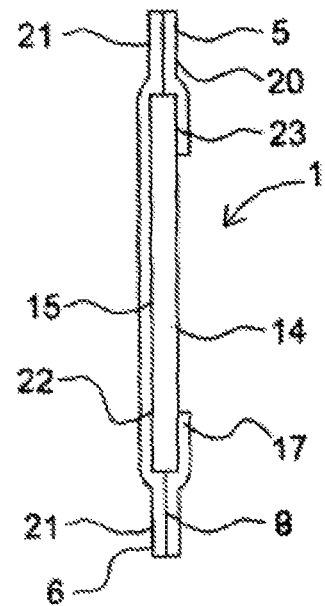
Figure 1(a)
Figure 1(b)
Figure 1(c)

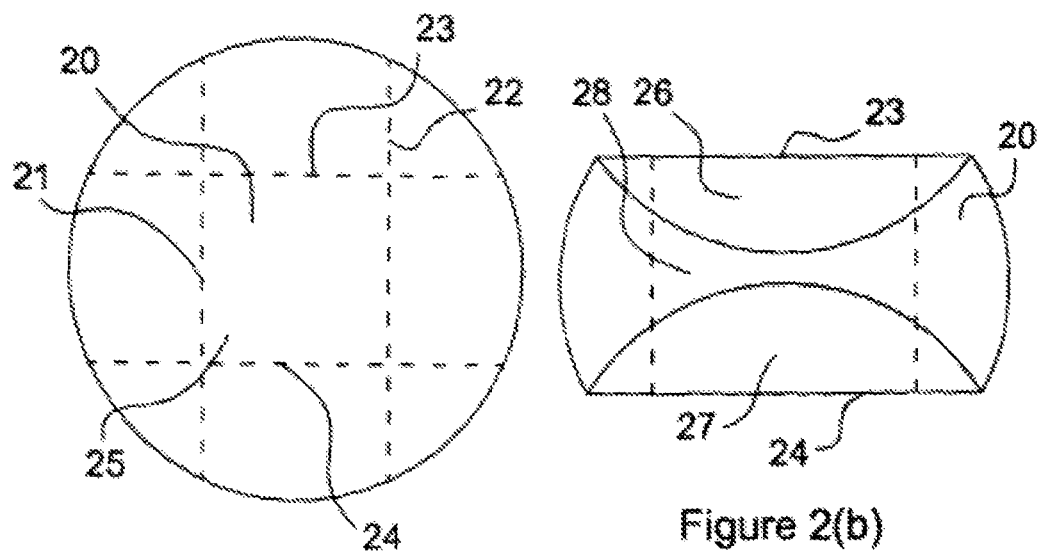
Figure 2(a)
Figure 2(b)
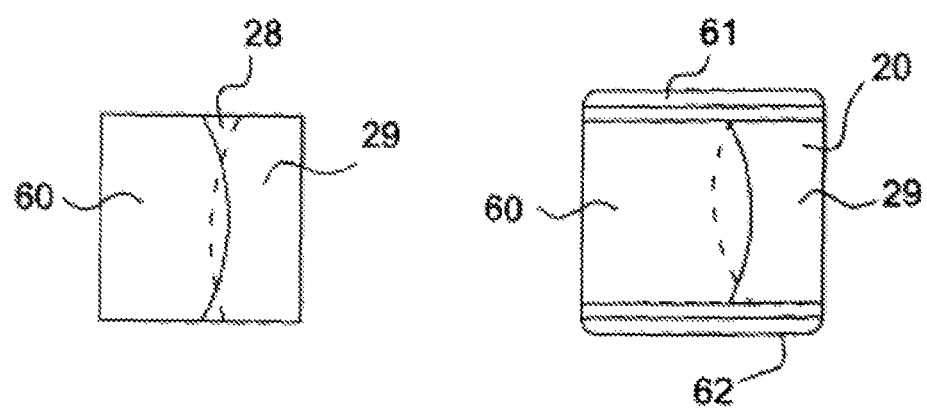
Figure 2(c)
Figure 2(d)

METHOD AND ASSEMBLY FOR PRINTING ONTO A BALLOON BLANK

CROSS REFERENCE TO RELATED APPLICATIONS

This application is a continuation-in-part application of, and claims the benefit of, PCT/GB2011/001751, entitled 'A Method of Printing onto a Balloon Blank' filed on Dec. 21, 2011, which claims the benefit of GB1021743.8 filed on Dec. 22, 2010, and GB1116672.5 filed on Sep. 28, 2011, all of which are incorporated by reference herein.

BACKGROUND OF THE INVENTION

Field of the Invention

The invention relates to balloon blanks, which are used in the process of printing an image onto an inflatable balloon. In particular, the invention relates to facilitating the printing of an image onto a balloon blank via a conventional computer-based ink jet or laser printer/printing means. In the context of this application the term "balloon blank" is to be interpreted broadly to incorporate a balloon with a primed, blank printing surface which is located about a supporting substrate. The printing surface of the balloon is held flat against the supporting substrate for receiving the image from an inkjet or laser printer.

Background

The closest prior art known to the Applicant includes U.S. Pat. No. 6,332,823 (Rouse), JP2008095886 (Daishin), U.S. Pat. No. 5,098,329 (Tseng), GB168292 (Thomas), U.S. Pat. No. 5,282,768 (Akman), U.S. Pat. No. 4,892,500 (Lau), U.S. Pat. No. 5,023,118 (Cheng), U.S. Pat. No. 4,929,215 (Lovik), U.S. Pat. No. 5,031,229 (Lovik), US2010/282625 and WO2009087352 (Lang) and the Applicant's own prior UK patent application GB0906198.7 all or most of which relate to balloon printing methods and assemblies.

The present invention concerns a method and assembly for printing an image onto a balloon's primed outer surface area via an inkjet printer or laser printer which addresses drawbacks of the prior art balloon printing methods and assemblies. Such drawbacks include the following.

The envelope of the balloon incorporates one or more fragile membranes, which can rip or tear when they come into contact with the rollers of a mechanism that drives the balloon blank through the inkjet printer/printing means. Furthermore, as the balloon blank is driven through the inkjet printer/printing means, the rollers stretch and distort the primed outer surface of the balloon, therefore the ink will not take to the surface of the balloon itself. A portion of the balloon blank is the leading edge that is exposed to subsequent grabbing, pinching and rolling from the drive mechanism, therefore causing damage to the surface of the balloon that may result in the balloon becoming separated from the balloon blank and becoming jammed within the drive mechanism. The optical sensors of an inkjet printer will generally not detect the presence of balloon blank because the envelope of the balloon is constructed from polymer-based materials or thermoplastic materials, therefore the printing process will not initiate. The trailing edge can be exposed to subsequent grabbing, pinching and rolling by the drive mechanism if the balloon is required to be transported in a second direction, which is opposite to the direction of the feeding mechanism of the inkjet/laser printers is a portion of the balloon blank.

In the prior art US2010/282625 (Lang) proposes that a cover sheet may be assembled overlying the underside of a balloon blank for printing in order to guard the under-folded edge parts of the balloon from risk of twisting/wrinkling when the balloon blank is transported through the printer. A leading edge of the superimposed cover sheet projects beyond the leading end of the balloon blank and serves as the lead into the printer. This arrangement addresses some of the problems of the prior art but it does not suit use in all printers and the use of a leading edge of the cover sheet as the lead into the printer can compromise uniformity of feeding through. We have also found that such arrangement is vulnerable to gaping of the layers of the balloon blank and substrate assembly and of the cover sheet which can cause feeding problems and smudging and the arrangement also does not protect the balloon blank for counter printing of the balloon blank in the reverse direction.

It is thus an aim of the present invention amongst other aims to address these and other problems of the prior art.

SUMMARY OF THE INVENTION

In a first broad independent aspect the invention provides a method of printing onto a balloon that comprises the steps of: coating the printable outer surface of a balloon with a primer material; attaching the balloon about a supporting substrate to form a balloon blank; flattening the printable outer surface of the balloon on the upper surface of the substrate; attaching a first tab on a first end of the balloon blank; attaching a second tab on a second end opposite the first end of the balloon blank; applying the balloon blank to a printer via the first tab, which in use prints a first image onto the printable surface;

The advantage of this approach is that it provides a simple and efficient method of printing an image stored in a conventional computer and then printing the image upon the balloon blank with minimal risk of jamming or of smudging the image. This method doesn't require any specialist printing skills or expensive equipment printing equipment. The balloon blank second tab minimizes gaping. Without such a second tab the layers of the balloon blank and substrate assembly and of the cover sheet can be prone to gape apart which can cause feeding problems and smudging. This may occur when the printer head is trapped between the gripping rollers and the balloon blank/substrate assembly is only gripped by the one front roller allowing the balloon edges to part which in turn can touch the print head and make lines or smudges on the printed image.

Preferably the method further comprises moving the balloon blank back through the printer via the second tab, which in use prints a second image onto the printable surface. The second tab can cooperate with the printing means to enable it to be passed through the printing means or a second printing means, so that a second image may be printed onto the balloon. This enables the balloon to cooperate with an ink jet or laser printer, whereby the printing of color images is achieved by feeding the balloon blank through the printer to overlay the required colors onto the image in forward and reverse passes. The two tab members prevent the balloon member of the balloon blank, from becoming damaged or getting caught up in the transport mechanisms of the printer/printing means.

In a related aspect of the invention, the invention provides a balloon blank comprising a first tab attached to a first edge of said balloon blank via a first attachment means, which in use, cooperates with a first mechanism of a printing means for inserting said balloon blank into said printing means via a first mechanism; wherein the balloon blank further comprises a second tab attached to a second edge of said balloon blank via a second attachment means, which in use, may cooperate with a second mechanism that transports said balloon blank within said printing means. The second tab further improves security of the balloon, blank and tabs assembly and helps to prevent gaping and risk of wrinkling and miss-feeding through the printer.

This enables a user to print an image, typically stored on computer, onto a balloon blank via a conventional printing means such as an ink jet or laser printer, therefore no specialist printing skill or printing equipment is required. The tab members enable the balloon blank to simulate a sheet of paper (typically A4 sized and shaped), whilst being loaded into the printing means. The feed and/or drive mechanism then moves the balloon blank through the printing means, typically via a pair of pinch rollers. The first tab member initially engages with the feed and/or drive mechanism before the leading edge of the balloon blank, thereby incurring any initial frictional contact with the feed and/or drive mechanism and therefore preserving the leading edge of the balloon blank. The second tab member engages with the drive of a second mechanism for taking up the trailing edge of the balloon, thereby enabling the movement of the balloon blank back into the printing means for facilitating the printing of colored images by overlaying the required images onto the image on the balloon.

The second tab member initially engages with the second drive mechanism before the trailing edge of the balloon blank, thereby incurring any initial frictional contact with the feed and/or drive mechanism and therefore preserving the trailing edge of the balloon blank.

Preferably the second edge of the balloon blank is opposite the first edge of the balloon blank. This enables the balloon blank to be transported in to the printer in a first direction and then subsequently transported back into the printer in the opposite direction for subsequent color printing.

Preferably, an upper most portion and lower most portion of said balloon blank are folded back on one face of said balloon blank; a right most portion and a left most portion of said balloon blank are folded back on said folded upper and lower most portions; said right and left most portions are secured to said face of said balloon blank via the attachment of said first and second tabs to said balloon blank. This configuration enables the balloon blank to be contained within a folded configuration, which does not allow the contained portions of the balloon to roll or slip whilst being pinched and rolled by the transport mechanisms of the printer. The two tabs maintain the exposed edges of the flat against the folded portions of the balloon underneath. The exposed edges of the balloon extend across the balloon blank between the two tabs, which prevent the balloon portions from moving or becoming unfolded from the balloon blank and potentially becoming entangled within the printer.

Preferably, each of said first and second tabs is a composite tab that comprises a first planar tab member and a second planar tab member, whereby each of said first planar tab member and second planar tab member cooperate to form a said composite tab about an edge of the balloon blank.

According to a further main aspect of the present invention there is provided a method of printing onto a balloon that comprises the steps of: coating the printable outer surface of a balloon with a primer material; attaching the balloon about a supporting substrate to form a balloon blank; flattening the printable outer surface of the balloon on the upper surface of the substrate; attaching a first composite tab having a first planar tab member and a second planar tab member to a first end of the balloon blank by attaching the first planar tab member to a first side of the first end of the balloon blank and the second tab member to a second side of the first end of the balloon blank to embrace or sandwich the first end therebetween and whereby the tab member lies substantially wholly within the plane of the balloon blank and projecting in that plane from the first end of the balloon blank; applying the balloon blank to a printer via the first tab, which in use prints a first image onto the printable surface. The tab is not an extension of a cover sheet and is not in a plane parallel tot overlying the plane of the balloon blank. It lies substantially wholly within the plane of the balloon blank, ie the plane between the opposing major, first and second, faces of the balloon blank. This approach facilitates feeding of the balloon blank and tab assembly through a printer assembly, mitigating risk of slippage or jamming and reducing risk of image tram-lining and smearing.

Preferably the first planar tab member and the second planar tab member are initially separate and the step of attaching the first composite tab to the balloon blank comprises adhering the first planar tab member to the first side of the first end of the balloon blank and the second tab member to the first planar tab member and to the second side of the first end of the balloon blank.

According to a related aspect of the present invention there is provided a balloon blank comprising a first tab attached to a first edge of said balloon blank via a first attachment means, which serves in use to cooperate with a first mechanism of a printer for inserting said balloon blank into said printer via a first mechanism, wherein the tab is a composite tab having a first planar tab member and a second planar tab member that attach to the balloon blank firmly embracing or sandwiching the first end therebetween and whereby the tab member lies substantially wholly within the plane of the balloon blank and projecting in that plane from the first end of the balloon blank.

Preferably the first and second planar tab members are initially formed separate of each other and each have a self-adhesive surface whereby the planar tab members are attached together and to the leading edge of the balloon blank to form the composite tab member about the leading edge.

In a further broad independent aspect the invention provides a balloon blank suitable for use with a printer, comprising a tape member which is attached to the surface of a first inflatable chamber and the surface of an adjacent second inflatable chamber, wherein said tape member induces a surface tension which pulls and holds said second inflatable chamber away from first inflatable member in an axial direction. This configuration prevents the second inflatable chamber from falling over the first inflatable chamber and therefore becoming unreadable or unrecognizable. This may due to under-inflation or distortion of the second inflatable chamber.

Preferably, a balloon blank further comprises a second tape member which is attached to the surface of said first inflatable chamber and said surface of said adjacent second inflatable chamber, whereby said second tape member is disposed on a side of said balloon blank which is substantially opposite said first tape member. This configuration enables the positioning of the second inflatable chamber relative to the first inflatable chamber, whereby the second inflatable chamber is supported on both sides.

Preferably, said tape member is attached to the surface of first inflatable chamber and the surface of said adjacent second inflatable chamber after an image has been printed onto the balloon. This enables the retro-fitting of the tape member of the balloon to support the second inflatable chamber relative to the first inflatable chamber.

The term printer used herein covers any printing machine whether having only a single printing head and transport mechanism or having multiple printing heads and transport mechanisms/multiple means of printing. It includes home/office printers as well as industrial printing systems.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Preferred embodiments of the present invention will now be more particularly described by way of example only with reference to the accompanying drawings, wherein:

FIG. 1a shows a schematic view of a balloon blank with two attached tab members in accordance with a preferred embodiment of the invention.

FIG. 1b shows a cross-sectional view of a balloon blank incorporating two attached tab members along two outer edges in accordance with the preferred embodiment of the invention.

FIG. 1c shows a cross-sectional view of a balloon blank incorporating two tab members along two outer edges in accordance with an alternative embodiment of the invention.

FIGS. 2a-2d show the four steps in the folding of a balloon which is required for a balloon blank.

Figure 3:
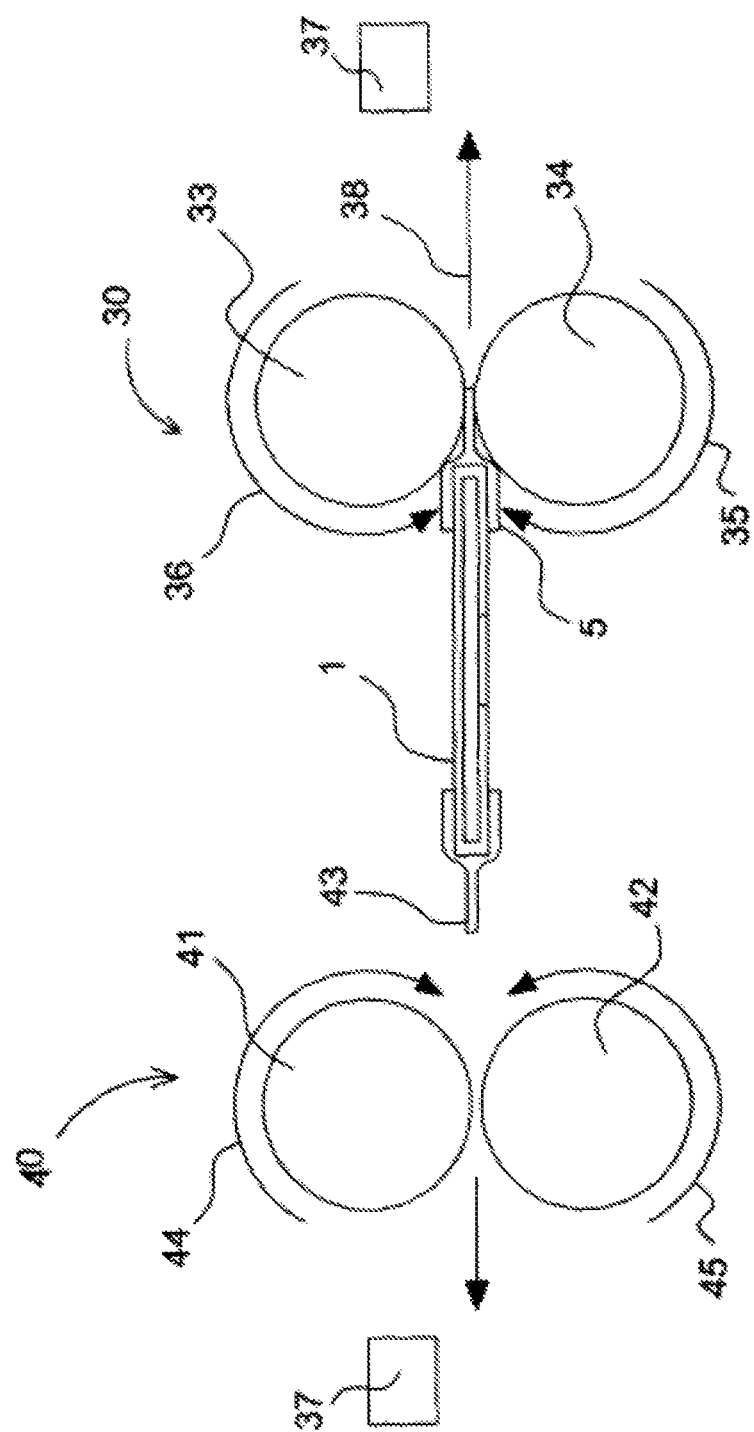

FIG. 3 shows a schematic view of a balloon blank, which is transferable in two directions via two printing mechanisms.

Figure 4:
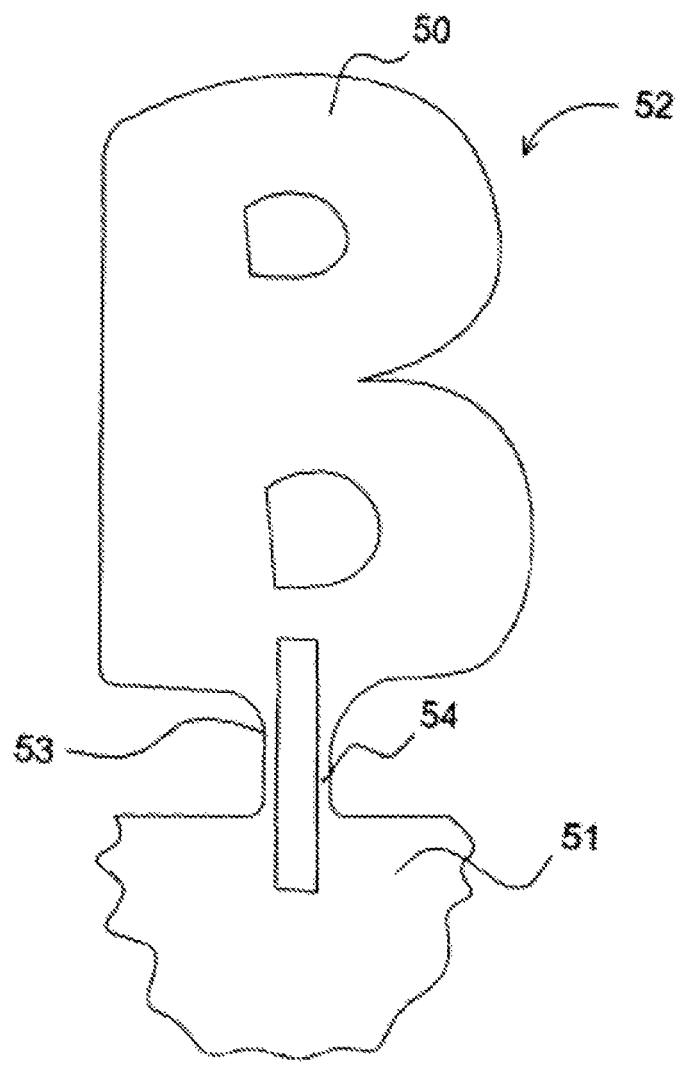

FIG. 4 shows a secondary view of a 'B' shaped secondary chamber being supported vertically from the primary chamber of the balloon.

Figure 5:
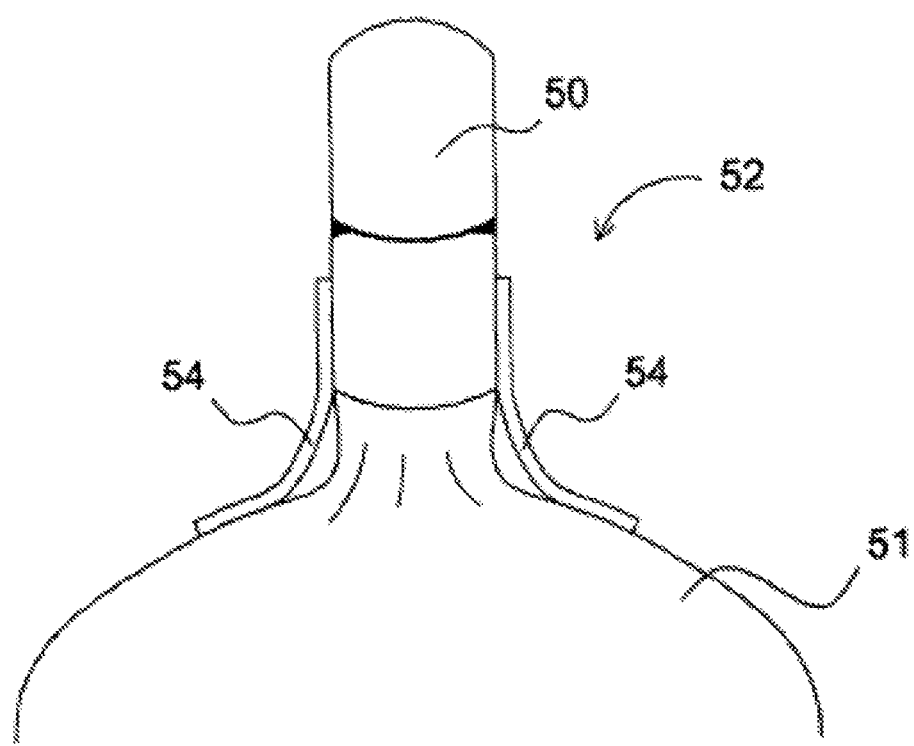

FIG. 5 shows a cross sectional view of a 'B' shaped secondary chamber being supported vertically from the primary chamber of the balloon by attached supporting members on either side.

Figure 6:
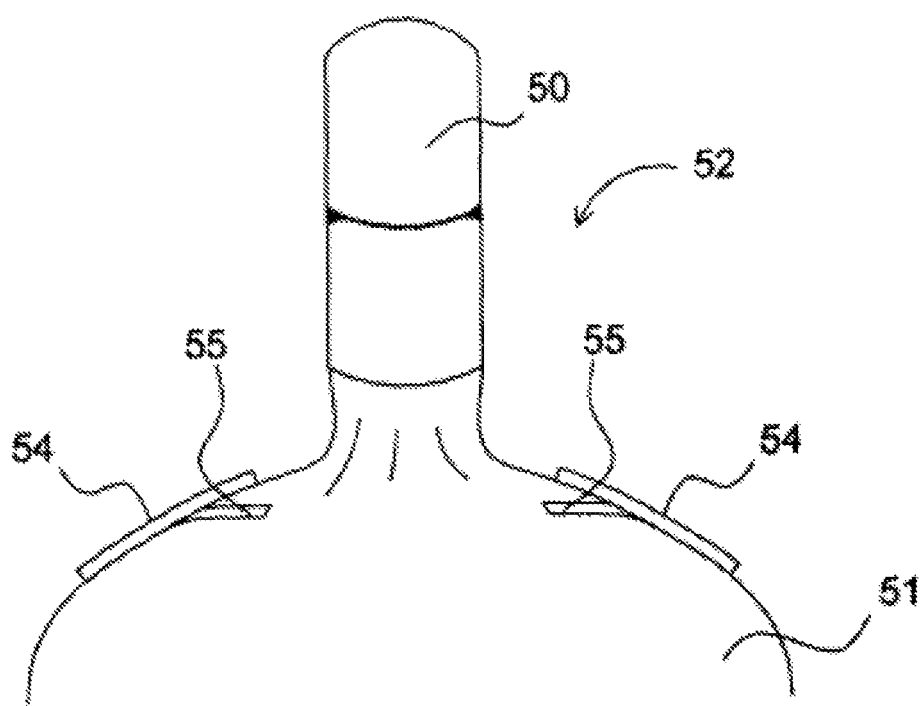

FIG. 6 shows a cross-sectional view of a "B" shaped secondary chamber being supported vertically from the primary chamber of the balloon whereby the primary chamber incorporates taped folds within its other surface.

DETAILED DESCRIPTION OF THE ILLUSTRATED EMBODIMENTS

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

FIG. 1a shows a schematic view of a rectangular balloon blank which is generally indicated by 1. The balloon blank 1 incorporates a balloon wrapped about a rectangular supporting substrate 3 and with the overlapped parts of the balloon adhered together and not to the substrate to hold it in place around the substrate. The rectangular outline of the supporting substrate is clearly shown. The balloon 2 is located about the supporting substrate 3, with the primed outer surface area 4 being located centrally on the supporting substrate 3.

A first tab 5 is attached to one edge of the balloon blank 1, typically the leading edge relative to the printer, such as an inkjet printer or laser printer. The first tab 5 extends substantially across the width of the balloon blank 5 along a horizontal axis AA. The first tab 5 incorporates directional indicators, which indicate the direction in which the balloon blank 1 is to be fed into the printer.

A second tab 6 is attached to a second edge of the balloon blank 1, which is opposite the leading edge with the first tab 5. The second tab 6 is typically a second trailing edge relative to the printer, which takes and transports the balloon blank 1 in a direction through the printer, which is different from the feeding direction to the printer, i.e. in the opposite direction back into or through the printer to print a second image onto the balloon, which is commonly used in colour printing techniques. The second tab 6 extends substantially across the width of the balloon blank 5 along horizontal axis AA. The second tab 6 further incorporates directional indicators, which indicate the direction in which the balloon blank 1 is taken up by a second mechanism of the printer.

FIG. 1b shows a cross-sectional view of the balloon blank 1 shown in FIG. 1a. The balloon blank has the first tab 5 located onto the leading edge. The first tab 5 is a composite tab formed by two elongate members 10 and 11, which are attached together about the leading edge of the balloon blank 1. The two elongate planar tab members 10 and 11 both incorporate a self-adhesive surface 12 and 13. The self-adhesive surface 12 of elongate member 10 is attached to the self-adhesive surface 13 of elongate member 11. The self adhesive surface 12 of elongate member 10 is also attached at one side 14 of the balloon blank 1. The self-adhesive surface 13 of elongate member 11 is attached to the opposite side 15 of the balloon blank 1. The outline shape of the elongate tab member 10 is symmetrical to the outline shape of elongate tab member 11, to form an overall shape for the first tab 5 (see FIG. 1*a*).

The balloon blank 1 also has a second tab 6 attached onto the trailing edge, which is opposite the leading edge of the balloon blank 1. The second tab member 6 is also composite, being formed by two elongate members 7 and 8, which are attached together about the trailing edge of the balloon blank 1. The two elongate members 7 and 8 both incorporate the self-adhesive surface 9 and 16. The self-adhesive surface 16 of elongate member 8 is attached to the self-adhesive surface 9 of elongate member 7. The self-adhesive surface 9 of elongate member 7 is also attached to one side 14 of the balloon blank 1. The self-adhesive surface 16 of elongate member 8 is attached to the opposite side 15 of the balloon blank 1. The outline shape of elongate member 7 is symmetrical to the outline shape of elongate member 8, to form an overall shape for the second tab 6. (See FIG. 1*a*).

FIG. 1*c* shows a cross-sectional view of the balloon blank 1 shown in FIG. 1*a* but here the balloon blank 1 is with an alternative embodiment of the first tab 5 and second tab 6. The first tab 5 incorporates two elongate members 20 and 21, which are attached together about the leading edge of the balloon blank 5. The two elongate members 20 and 21 both incorporate a self-adhesive surface 22 and 23, which are attached together to the balloon blank as described in FIG. 1*b*. The elongate member 21 is different from that in FIG. 1(*b*) since it extends as a planar sheet like a cover sheet substantially over the entirety of one side 15 of the balloon blank 1. The self adhesive surface 22 also extends substantially over that side 15 of the balloon blank 1. The extended elongate member 22 secures the drape portions of the balloon wrapped about the supporting substrate, within the balloon blank 1, therefore preventing any unsecured portion of the balloon from becoming jammed within the feed mechanism or second transportation mechanism of the printer.

The second tab 6 is also a composite tab and incorporates elongate member 21 and elongate member 17, which are attached together about the trailing edge which is opposite the leading edge of the balloon blank 1. Elongate member 17 incorporates a self-adhesive surface 18 which is attached to the self-adhesive surface 22 of elongate member 21 and to the balloon blank 1 as shown in FIG. 1*b*.

In use, a protective cover is removed from one of the elongate members that form the first tab to expose the self-adhesive surface underneath. The elongate tab member is then attached to one side of the leading edge of the balloon blank. The protective cover is then removed from a second symmetrical elongate tab member to expose the self-adhesive surface underneath. The second elongate member is then attached to the opposite side of the leading edge of the balloon blank. The two self adhesive surfaces of the two elongate members are then attached together to form a first overall tab member about the leading edge. The first tab member provides a protective cover to the leading edge of the balloon blank, which prevents damage from occurring to the surface of the balloon blank when it is passed through the feed mechanism of a printer. The elongate tab members are formed from a substantially wood pulp based material such as paper or cardboard or the like. This enables the sensors within the printer, which are typically optical sensors, to detect the presence of the balloon blank and then initiate the feed and printing processes of the printer. If the first tab member was absent, or was constructed from another material, it would be very likely that the sensor wouldn't detect the presence of the balloon blank.

A protective cover is removed from one of the elongate members that forms the second tab to expose a self-adhesive surface underneath. The elongate tab member is then attached to one side of the trailing edge of the balloon blank. The protective cover is removed from a second symmetrical elongate tab member to expose a self-adhesive surface underneath. The second elongate member is then attached to the opposite side of the trailing edge of the balloon blank. The two self-adhesive surfaces of the two elongate members are then attached together to form the second tab about the trailing edge of the balloon blank. The second tab provides a protective cover to the trailing edge of the balloon blank, which prevents damage from occurring to the surface of the balloon blank when it is passed through the mechanism of the printer, by the balloon blank's trailing edge. The elongate members of the second tab are also formed from a wood-based material, for the same reasons as the first tab member.

In an alternative embodiment of the invention the second tab may be attached on an edge which is not opposite the leading edge of the balloon blank. Therefore, the second tab may be attached to an edge which extends in a direction which is different from the direction of the leading edge of the balloon blank.

FIGS. 2*a* to 2*d* show the four steps required to fold a balloon 20 in to a small four sided configuration, which is required for containing the balloon 20 within a balloon blank. FIG. 2*a* shows the balloon 20 incorporates two parallel fold lines 21 and 22 that extend vertically across the balloon. Both vertical fold lines 21 and 22 maintain the same spacing from each other across their entire lengths. The balloon 20 further incorporates two parallel fold lines 23 and 24 that extend horizontally across the balloon 20. Both horizontal fold lines 23 and 24 maintain the same spacing from each other across their entire lengths. An upper portion of vertical fold line 21 intersects with a left portion of horizontal line 23. An upper portion of vertical fold line 22 intersects with a right portion of horizontal line 23. A lower portion of vertical fold line 21 intersects with a left portion of horizontal line 24. A lower portion of vertical fold line 22 intersects with a right portion of horizontal line 24. Therefore, the fold lines 21 to 24 intersect each other to form an outline for a four sided shape 25, such as a square, rectangle or the like.

FIG. 2*b* shows a substantially square or rectangular supporting substrate 28 located at the center of the balloon 20. An upper portion 26 of the balloon 20 is folded over the supporting substrate 28 via horizontal fold line 23. A lower portion 27 of the balloon 20 is folded over the supporting substrate of the balloon, via horizontal fold line 24 and therefore forming the upper and lower edges of the balloon blank.

FIG. 2*c* shows a right portion 29 of the balloon 20 folded over the supporting substrate 28 via vertical fold line 22. A left portion 60 of the balloon is folded over the supporting substrate 28 via vertical fold line 21. The left portion 60 of the balloon incorporates a portion that overlaps the right portion 29 of the balloon 20, which forms the right and left edges of the balloon blank. The exposed edges of the right and left portions 29 and 60 are curved towards the center of the balloon 20. The overlapped portions of the balloon 20 are adhered together to hold the balloon 20 in place wrapped about the substrate.

FIG. 2*d* shows an upper tab member 31 and a lower tab member 32, which are fixed to the folded right 29 and left 60 portions of the balloon 20. The upper and lower tab members 61 and 62 respectively serve to maintain the balloon 20 in folded configuration about the supporting substrate. The upper tab member is fed into the take up mechanism of a printer such as an ink jet or laser printer. The take up mechanism will grab and roll the folded portions 60 and 29 of the balloon 20, via rollers that extend laterally across the balloon blank as it applied to the printer. As the exposed edges of the balloon 20 extend vertically over the supporting substrate, they do not move or get displaced when the balloon blank becomes engaged with the take up mechanism. This, therefore, prevents the balloon 20 from getting caught or snagged within the mechanisms of the printer, which may cause damage to the balloon 20 and/or to the printer.

FIG. 3 shows a schematic view of a balloon blank 1 as shown in FIGS. 1a-1c. The balloon blank 1 is applied to the printer generally indicated by 30, which may incorporate a conventional inkjet or laser printer mechanism 37. The balloon blank 1 is then lifted and inserted into a first printer 30, as if it were a conventional sheet of paper as indicated by arrow 38. The balloon blank is then clasped between two rollers 33 and 34 via the tab 5, one of the rollers 33 or 34 being a driven pinch roller. As the pinch roller passes the balloon blank 1 through the first printer 30, it grips only the tab 5 therefore preventing any direct contact to the leading edge of the balloon blank itself 1. The direction of rotation of each of the rollers 33 and 34 is indicated by arrows 35 and 36. The tab 5 projecting in the plane of the balloon blank prevents any distortion of the image and any possible jamming of the printer that may cause damage to the balloon.

The balloon blank is re-applied to the printing mechanism 37, or a second printing mechanism 40. The balloon blank 1 may be lifted and inserted into the second printing mechanism, generally indicated by 40. The balloon is there clasped between two rollers 41 and 42 via the second tab 43, one of the rollers 41 or 42 being driven as a pinch roller. As the pinch roller passes the balloon blank 1 through the printing mechanism 37, it grips only the second tab 43. It, therefore, prevents any direct contact with the trailing edge of the balloon blank itself. The direction of rotation of each of the rollers 41 and 42 is indicated by arrows 44 and 45. The tabs 43 prevent any damage to the balloon in the take-up of the trailing edge, while the balloon blank is being re-applied to the printer for printing a second image onto the surface of the balloon blank.

FIG. 4 shows a schematic view of a "B" shaped secondary chamber 50 connected to a portion of primary chamber 51 of a novelty balloon 52. The secondary chamber 50 may be in the form of a character or number, when inflated. The secondary chamber 50 incorporates at least one passageway 53, which communicates fluid, such as air or helium gas, from the primary chamber 51 of the novelty balloon 52. The secondary chamber 50 is subsequently inflated when the primary chamber 51 is inflated. A supporting member 54 supports a secondary chamber 50 in a vertical position away from the primary chamber 51, therefore enabling the inflated secondary chamber 50 to be easily read. If the secondary chamber 50 is unsupported, it would fall back on itself and would therefore be hard to read. The supporting member 54 is typically formed from a strip of material which is light and flexible which will not cause damage to either the secondary or primary balloon chambers of the balloon. The supporting material is typically formed from a film or plastic tape, which incorporates a self-adhesive material coated on one side. The supporting member 54 is then attached to the balloon 52 by placing it onto the passageway which connects the primary and secondary chambers 40 and 41 of the balloon together.

The tape, whilst attached to the balloon, prevents the surface of the balloon from increasing when the balloon is inflated. This has the effect of pulling the secondary chamber vertical relative to the primary chamber.

FIG. 5 shows a cross-sectional view of the secondary chamber 50 and primary chamber 51 of a novelty balloon 52. This configuration is shown in FIG. 4. The supporting member 54 is attached to the outer surfaces of the primary chamber 51 and the secondary chamber 50 on opposite sides of the balloon. When the balloon is inflated the outer surface of the primary chamber 51 expands and causes the attached supporting device 54 on either side of the balloon, to pull the secondary chamber 50 up an upwards direction. This maintains the vertical chamber in an erect vertical position, which does not collapse to either side.

FIG. 6 shows an alternative cross-sectional view of the second chamber 50 and primary chamber 51 of a novelty balloon 52, as shown in FIGS. 4 and 5. The balloon 52 incorporates a fold 55 within the outer surface of the primary chamber 51, in each of its opposing sides. The folds 55 reduce the surface area of the balloon 52, which reduces the height of the primary chamber 51 and therefore the overall height of the balloon. Each fold is covered by a supporting member 54 (as described in FIG. 5), which is adhered to the outer surface of the balloon 52, over the fold on each of the opposing sides of the primary chamber 51.

In other aspects the invention provides a balloon blank for use with a printer, comprising a tape member which is attached to the surface of a first inflatable chamber and the surface of an adjacent second inflatable chamber, wherein said tape member induces a surface tension which pulls and holds said second inflatable chamber away from first inflatable member in an axial direction. The balloon blank here may further comprise a second tape member which is attached to the surface of said first inflatable chamber and said surface of said adjacent second inflatable chamber, whereby said second tape member is disposed on a side of said balloon blank which is substantially opposite said first tape member. The said tape member is suitably attached to the surface of the first inflatable chamber and the surface of said adjacent second inflatable chamber after an image has been printed onto the balloon.

In a further other aspect the invention may provide a balloon blank for use with a printer, comprising a first inflatable chamber and an adjacent second inflatable chamber, wherein two opposing sides of the surface of the primary chamber each incorporates a folded portion, which is covered by an attached supporting member; in use, said supporting member provides a surface tension which pulls and holds the second inflatable chamber away from the first inflatable member in an axial direction.

The present invention embraces a method of printing onto a balloon substantially as hereinbefore described and/or illustrated in the accompanying text and/or FIGS. 1 to 6 and also a tab and a balloon blank substantially as hereinbefore described and/or illustrated in the accompanying text and/or FIGS. 1 to 6.

The embodiments described above are only example, preferred embodiments of the invention and do not limit the claims of the present invention. All equivalent substitutions and modifications may be made without departing from the spirit and scope of the present invention and should be viewed as embraced in the appended claims.

What is claimed is:

1. A balloon blank comprising:
   a. a first tab attached to a first edge of a balloon blank via a first attachment means, which serves in use to cooperate with a first mechanism of a printer for inserting said balloon blank into said printer via a first mechanism; and
   b. a second tab attached to a second edge of said balloon blank via a second attachment means, wherein the first and second tab are not directly linked, and a planar sheet does not cover at least one folded edge on a face away from a face that is printed.

2. The balloon blank of claim 1, wherein the second tab serves in use to cooperate with a second mechanism that transports the balloon blank within said printer.

3. The balloon blank of claim 1, wherein the second edge of the balloon blank is opposite the first edge of the balloon blank.

4. The balloon blank of claim 1, wherein an upper most portion and lower most portion of the balloon blank are folded back on one face of said balloon blank; a right most portion and a left most portion of said balloon blank are folded back on said folded upper and lower most portions; and said right and left most portions are secured to said face of said balloon blank via the attachment of said first and second tabs to said balloon blank.

5. The balloon blank of claim 1, wherein each of the first and second tabs further comprises an attachable tab member, whereby each of said first and second tabs cooperates with said attachable tab member to form an overall tab about the first and second edges of the balloon blank.

6. The balloon blank of claim 1, wherein the balloon blank comprises a balloon wrapped about a supporting substrate, wherein overlapping parts of the balloon are adhered to each other, and not to the substrate, to hold the balloon blank in place around the substrate.

7. A balloon blank comprising:
   a. a first tab attached to a first edge of a balloon blank via a first attachment means, which serves in use to cooperate with a first mechanism of a printer for inserting said balloon blank into said printer via said first mechanism, wherein said first tab is a composite tab having a first planar tab member and a second planar tab member that are configured to attach to said balloon blank firmly embracing or sandwiching said first edge therebetween and whereby said first tab member lies substantially wholly within a plane of the balloon blank and projects in that plane from said first end of said balloon blank;
   b. a second tab attached to a second edge of said balloon blank via a second attachment means, wherein the first and second tab are not directly linked and the balloon blank has no planar sheet covering at least one folded edge of said balloon blank on a face away from a face that is printed.

8. The balloon blank of claim 7, wherein the first and second planar tab members each have a self-adhesive surface whereby the first and second planar tab members are adhered and attached together and adhered to and attached a leading edge of said balloon blank to form said composite tab about said leading edge.

9. The balloon blank of claim 7, wherein the balloon blank comprises a balloon wrapped about a supporting substrate creating a plurality of overlapping parts of said balloon that are adhered to each other, and not to the substrate, to hold said balloon blank in place around said supporting substrate.

* * * * *